United States Patent
Cho et al.

(10) Patent No.: US 7,751,694 B2
(45) Date of Patent: *Jul. 6, 2010

(54) THREE-DIMENSIONAL ENDOSCOPE IMAGING AND DISPLAY SYSTEM

(75) Inventors: Gyoung Il Cho, Seoul (KR); Sang Hyune Baek, Suwon (KR); Cheong Soo Seo, Seongnam (KR)

(73) Assignees: Angstrom, Inc., Scongnam (KR); Stereo Display, Inc., Anaheim, CA (US)

( * ) Notice: Subject to any disclaimer, the term of this patent is extended or adjusted under 35 U.S.C. 154(b) by 773 days.

This patent is subject to a terminal disclaimer.

(21) Appl. No.: 11/314,408

(22) Filed: Dec. 20, 2005

(65) Prior Publication Data

US 2006/0120706 A1 Jun. 8, 2006

Related U.S. Application Data

(63) Continuation-in-part of application No. 10/983,353, filed on Nov. 8, 2004, now Pat. No. 7,267,447, and a continuation-in-part of application No. 10/979,624, filed on Nov. 2, 2004, now Pat. No. 7,261,417, and a continuation-in-part of application No. 10/893,039, filed on Jul. 16, 2004, now Pat. No. 7,239,438, and a continuation-in-part of application No. 10/872,241, filed on Jun. 18, 2004, now Pat. No. 7,382,516, and a continuation-in-part of application No. 10/822,414, filed on Apr. 12, 2004, now Pat. No. 7,068,416, and a continuation-in-part of application No. 10/778,281, filed on Feb. 13, 2004, now Pat. No. 7,077,523.

(51) Int. Cl.
*A61B 1/04* (2006.01)

(52) U.S. Cl. ..................................................... 396/17

(58) Field of Classification Search .................. 396/17; 348/45, 65, 73, 75; 600/109, 111

See application file for complete search history.

(56) References Cited

U.S. PATENT DOCUMENTS

| | | | |
|---|---|---|---|
| 2,002,376 A | 5/1935 | Mannheimer | |
| 3,520,587 A | 7/1970 | Tasaki et al. | |
| 4,407,567 A | 10/1983 | Michelet | |
| 4,834,512 A | 5/1989 | Austin | |
| 5,004,319 A | 4/1991 | Smither | |
| 5,212,555 A | 5/1993 | Stoltz | |
| 5,307,170 A * | 4/1994 | Itsumi et al. | 348/219.1 |
| 5,369,433 A | 11/1994 | Baldwin | |
| 5,402,407 A | 3/1995 | Eguchi et al. | |

(Continued)

FOREIGN PATENT DOCUMENTS

JP 08-043881 2/1996

(Continued)

OTHER PUBLICATIONS

Boyd et al., "Fast-response Variable Focusing Micromirror Array Lens", 2003 (date), SPIE, vol. 50555, pp. 278-286.*

*Primary Examiner*—W. B. Perkey

(57) ABSTRACT

The present invention provides a three-dimensional endoscope system comprising a three-dimensional imaging device and a three-dimensional display device using a variable focal length micromirror array lens. The micromirror array lens has enough focusing speed and focusing depth range for three-dimensional imaging and realistic three-dimensional display.

30 Claims, 12 Drawing Sheets

U.S. PATENT DOCUMENTS

| | | |
|---|---|---|
| 5,467,121 A | 11/1995 | Allcock |
| 5,612,736 A | 3/1997 | Vogeley et al. |
| 5,673,147 A | 9/1997 | McKinley |
| 5,696,619 A | 12/1997 | Knipe |
| 5,751,341 A | 5/1998 | Chaleki et al. |
| 5,881,034 A | 3/1999 | Mano |
| 5,897,195 A | 4/1999 | Choate |
| 5,986,811 A | 11/1999 | Wohlstadter |
| 6,025,951 A | 2/2000 | Swart |
| 6,028,689 A | 2/2000 | Michaliek |
| 6,064,423 A | 5/2000 | Geng |
| 6,084,843 A | 7/2000 | Abe |
| 6,104,425 A | 8/2000 | Kanno |
| 6,111,900 A | 8/2000 | Suzudo |
| 6,123,985 A | 9/2000 | Robinson |
| 6,282,213 B1 | 8/2001 | Gutin et al. |
| 6,288,767 B1 * | 9/2001 | Murata et al. ............... 349/200 |
| 6,315,423 B1 | 11/2001 | Yu |
| 6,329,737 B1 | 12/2001 | Jerman |
| 6,498,673 B1 | 12/2002 | Frigo |
| 6,503,195 B1 * | 1/2003 | Keller et al. ............... 600/160 |
| 6,507,366 B1 | 1/2003 | Lee |
| 6,549,730 B1 | 4/2003 | Hamada |
| 6,563,105 B2 | 5/2003 | Seibel et al. |
| 6,625,342 B2 | 9/2003 | Staple et al. |
| 6,649,852 B2 | 11/2003 | Chason et al. |
| 6,650,461 B2 | 11/2003 | Atobe et al. |
| 6,658,208 B2 | 12/2003 | Watanabe et al. |
| 6,711,319 B2 | 3/2004 | Hoen |
| 6,741,384 B1 | 5/2004 | Martin |
| 6,749,346 B1 | 6/2004 | Dickensheets et al. |
| 6,784,771 B1 | 8/2004 | Fan |
| 6,798,570 B1 | 9/2004 | Greenberg |
| 6,833,938 B2 | 12/2004 | Nishioka |
| 6,885,819 B2 | 4/2005 | Shinohara |
| 6,900,901 B2 | 5/2005 | Harada |
| 6,900,922 B2 | 5/2005 | Aubuchon |
| 6,906,848 B2 | 6/2005 | Aubuchon |
| 6,906,849 B1 | 6/2005 | Mi |
| 6,914,712 B2 | 7/2005 | Kurosawa |
| 6,919,982 B2 | 7/2005 | Nimura et al. |
| 6,934,072 B1 | 8/2005 | Kim |
| 6,934,073 B1 | 8/2005 | Kim |
| 6,943,950 B2 | 9/2005 | Lee |
| 6,949,069 B2 | 9/2005 | Farkas et al. |
| 6,958,777 B1 | 10/2005 | Pine |
| 6,970,284 B1 | 11/2005 | Kim |
| 6,995,909 B1 | 2/2006 | Hayashi et al. |
| 6,999,226 B2 | 2/2006 | Kim et al. |
| 7,023,466 B2 | 4/2006 | Favalora et al. |
| 7,031,046 B2 | 4/2006 | Kim et al. |
| 7,046,447 B2 | 5/2006 | Raber et al. |
| 7,068,416 B2 | 6/2006 | Gim et al. |
| 7,077,523 B2 | 7/2006 | Seo et al. |
| 7,161,729 B2 | 1/2007 | Kim et al. |
| 7,212,330 B2 * | 5/2007 | Seo et al. ............... 359/298 |
| 2002/0018407 A1 | 2/2002 | Komoto |
| 2002/0102102 A1 | 8/2002 | Watanabe |
| 2002/0135673 A1 | 9/2002 | Favalora |
| 2003/0058520 A1 | 3/2003 | Yu |
| 2003/0071125 A1 | 4/2003 | Yoo |
| 2003/0174234 A1 | 9/2003 | Kondo |
| 2003/0184843 A1 | 10/2003 | Moon |
| 2004/0009683 A1 | 1/2004 | Hiraoka |
| 2004/0012460 A1 | 1/2004 | Cho |
| 2004/0021802 A1 | 2/2004 | Yoshino |
| 2004/0052180 A1 | 3/2004 | Hong |
| 2004/0246362 A1 | 12/2004 | Konno |
| 2004/0252958 A1 | 12/2004 | Abu-Ageel |
| 2005/0024736 A1 | 2/2005 | Bakin |
| 2005/0057812 A1 | 3/2005 | Raber |
| 2005/0136663 A1 | 6/2005 | Terence Gan et al. |
| 2005/0174625 A1 | 8/2005 | Huiber |
| 2005/0180019 A1 | 8/2005 | Cho |
| 2005/0212856 A1 | 9/2005 | Temple |
| 2005/0224695 A1 | 10/2005 | Mushika |
| 2005/0225884 A1 | 10/2005 | Gim |
| 2005/0231792 A1 | 10/2005 | Alain |
| 2005/0264870 A1 | 12/2005 | Kim |
| 2006/0012766 A1 | 1/2006 | Klosner |
| 2006/0012852 A1 | 1/2006 | Cho |
| 2006/0028709 A1 | 2/2006 | Cho |
| 2006/0187524 A1 | 8/2006 | Sandstrom |
| 2006/0209439 A1 | 9/2006 | Cho |

FOREIGN PATENT DOCUMENTS

| | | |
|---|---|---|
| JP | 11-069209 | 3/1999 |
| JP | 2002-288873 | 10/2002 |

* cited by examiner

THREE-DIMENSIONAL ENDOSCOPE IMAGING AND DISPLAY SYSTEM

REFERENCES TO RELATED APPLICATIONS

This application is a continuation-in-part of, and claims priority to U.S. patent application Ser. No. 10/778,281 filed Feb. 13, 2004, U.S. patent application Ser. No. 10/822,414 filed Apr. 12, 2004, and U.S. patent application Ser. No. 10/979,624 filed Nov. 2, 2004, U.S. patent application Ser. No. 10/983,353 filed Nov. 8, 2004, U.S. patent application Ser. No. 10/872,241 filed Jun. 18, 2004, U.S. patent application Ser. No. 10/893,039 filed Jul. 16, 2004, all of which are hereby incorporated by reference.

FIELD OF INVENTION

The present invention relates to endoscope systems, and in particular, a three-dimensional endoscope system comprising a real-time three-dimensional imaging device and a three-dimensional display device.

BACKGROUND OF INVENTION

An endoscope is a minimal invasive imaging instrument having a rigid or flexible long narrow tube shape, allowing viewing an internal structure of a body through a natural opening or a small incision for clinical inspection and treatment. Typically, endoscopes comprise the lens system, a light and image delivery system such as relay lens or optical fibers, an imaging system, various channels for treatment tool passage, and a display system.

Endoscopic procedures require precise hand-eye coordination and minute manipulation, which can be hardly accomplished by monocular vision. Three-dimensional vision provides more informative and intuitive observation of scene and precise interaction with environment than monocular vision does. Thus, it has become an indispensable element for the endoscope system.

Three-dimensional vision can be accommodated by binocular parallax, motion parallax, confocal scanning, structured light depth extraction techniques, and the like.

U.S. Pat. No. 3,520,587 to Tasaki discloses a stereoscopic endoscope having two objective lens systems with two fiber optic image delivery systems to provide a pair of stereoscopic images. U.S. Pat. No. 5,751,341 to Chaleki and U.S. Pat. No. 5,673,147 to McKinley also disclose systems and methods to provide a pair of stereoscopic images for endoscopes. However, a binocular vision system can cause eye-strain and fatigue for prolonged uses, and requires special eye-wear to see three-dimensional images. Also, it is difficult to design a compact endoscope system without degrading the image quality because the binocular vision system uses multiple camera systems and image delivery systems within the limited space.

U.S. Pat. No. 6,798,570 to Greenberg discloses a three-dimensional imaging and reconstruction system with a single camera system using motion parallax. In this system, the camera system must be continuously moving to generate three-dimensional effect, which can make inspection and treatment procedures complicated and cause trauma to a patient.

U.S. Pat. No. 6,949,069 to Farkas discloses a three dimensional confocal system in which a point of interest is illuminated by a light source using pinhole apertures. The confocal system can provide a high resolution three-dimensional image with a single camera system, but most of illuminating light is wasted and causes noise problem. To overcome this, U.S. Pat. No. 6,749,346 to Dickensheets and U.S. Pat. No. 6,563,105 to Seibel use a single optical fiber to scan and collect reflected light, but point by point scanning can lead to a slow image refresh rate.

U.S. Pat. No. 6,503,195 to Keller discloses a structured light depth extraction system in which a projector projects a structured light pattern such as grids in the visible or invisible form onto an object, and then an image processor calculates the depth information based on the reflected light pattern. In case of using visible light, image quality can be degraded while using invisible light requires an additional sensor system. Also, performance of the structured light depth extraction system depends on the reflectivity of the object.

Conventional endoscope systems usually use a wide field of view; typically, about 70 degree. A wide field of view is useful for viewing an overall internal structure and spotting an area of interest, but it may not provide enough information for diagnosis or treatment because the image produced by the wide field of view tends to suffer from huge distortion and low resolution. A narrow field of view produces a better quality and higher resolution image, and facilitates diagnosis and treatment. A desirable endoscope system must provide both wide and narrow fields of view.

A variable magnification (or a variable field of view) can be accomplished by changing relative locations of lenses in multiple lens system like a zoom lens system. However, it requires complicated macroscopic servo mechanism and yields a slow response time.

Also, conventional endoscope systems have a fixed line of sight along a longitudinal axis of an endoscope body while the area of interest rarely lies on the center thereof. The variable optical axis imaging system without macroscopic reposition or rotation of the endoscope body can benefit a patient by reducing unnecessary contact between lesion and the instrument.

The minimal invasive nature of endoscopic procedures requires the tube with a small diameter to reduce the size of incision and patient's trauma, sharp three-dimensional video images since a clinician can not see an object directly, a wide field of view for surveying the area of interest, a narrow field of view with high resolution images for inspection and treatment, and a variable optical axis to view the surrounding area without macroscopic movements of an endoscope body or parts thereof.

SUMMARY OF INVENTION

The present invention provides a three-dimensional endoscope system comprising a three-dimensional imaging device and a three-dimensional display device using a variable focal length micromirror array lens (MMAL).

An objective of the invention is to provide a three-dimensional imaging device that generates in-focus depthwise images with depth information or an all-in-focus image with depth information of each pixel.

The three-dimensional imaging device comprises at least one camera system having a lens system including at least one variable focal length MMAL, an objective lens, and auxiliary lenses, an imaging unit, an image processing unit, and a light delivery system.

The variable focal length MMAL comprises a plurality of micromirrors. The following U.S. patents and applications describe the MMAL: U.S. Pat. No. 6,934,072 to Kim , U.S. Pat. No. 6,934,073 to Kim , U.S. Pat. No. 6,970,284 to Kim , U.S. patent application Ser. No. 10/855,715 filed May 27, 2004, U.S. patent application Ser. No. 10/857,714 filed May 28, 2004, U.S. patent application Ser. No. 10/857,280 filed May 28, 2004, U.S. patent application Ser. No. 10/893,039 filed Jul. 16, 2004, U.S. patent application Ser. No. 10/983,353 filed Nov. 8, 2004, all of which are hereby incorporated by reference.

The variable focal length MMAL is suitable for the three-dimensional imaging and display device of the present invention since it has a fast focusing speed and a large range of focal length, and since it can be made to have a small or large aperture.

The imaging unit includes one or more two-dimensional image sensors taking two-dimensional images at different focal planes. The detail for three-dimensional imaging using the variable focal length MMAL can be found in U.S. patent application Ser. No. 10/822,414 filed Apr. 12, 2004, U.S. patent application Ser. No. 10/979,624 filed Nov. 2, 2004, and U.S. patent application Ser. No. 11/208,115 filed Aug. 19, 2005.

The image sensor takes two-dimensional images of an object or scene with one or more focal planes that are shifted by changing the focal length of the variable focal length MMAL. The image processing unit extracts substantially in-focus pixels or areas from each two-dimensional image to generate a corresponding in-focus depthwise image. Based on the known focal length of the two-dimensional image, depth information of the corresponding in-focus depthwise image can be obtained. Each in-focus depthwise image represents a portion of the object having the same image depth. The focal length of the variable focal length MMAL can progressively increase or decrease, or varies in a selected order within a focal length variation range of the variable focal length MMAL such that any portion of the object or scene is imaged substantially in-focus at least once. A set of in-focus depthwise images taken at different focal lengths with a fast imaging rate represents the object or scene at a given moment. The object can remain still or be moving. For the case that the object is moving, the movement of the object can be ignored when the imaging rate is fast enough. The number of in-focus depthwise images representing the object at a given moment (number of depths) depends on the depth resolution requirement, and the refresh rate of the two-dimensional display and the focusing speed of the variable focal length MMAL, and may increase for a better image quality. There are several methods for the image processing unit to generate an all-in-focus image of the object or scene from in-focus depthwise images thereof. Recent advances in both the image sensor and the image processing unit make them as fast as they are required to be. Depth information of each pixel of the all-in-focus image can be obtained in the same way as the depthwise image case. All the processes are achieved within a unit time which is at least persistent rate of the human eye.

A set of depthwise images with depth information or an all-in-focus image with depth information can be displayed by various conventional three-dimensional display devices through geometric data transformation. The present invention includes a three-dimensional display device, which displays these images without data transformation, as explained below.

Another objective of the invention is to provide the imaging device with a variable magnification (a variable field of view) in order to allow a microscopic observation. It is efficient and desirable to use a wide field of view with lower resolution images for viewing an overall internal structure and spotting an area of interest, and a narrow field of view with higher resolution images for diagnosis and treatment. The variable focal length MMAL of the present invention has a large range of focal length variation, which can offer a variable field of view; a shorter focal length for a wider field of view and a longer focal length for a narrow field of view. The field of view is changed without macroscopic movements of the lens system because each micromirror of the variable focal length MMAL is adjusted for varying the focal length and actuated by the electrostatic force and/or electromagnetic force.

Still another objective of the invention is to provide an imaging device having a variable optical axis without macroscopic movements of an endoscope body or parts thereof in order to center the object of interest in the image plane. In the present invention, the optical axis of the variable focal length MMAL can be adjusted in a limited range by controlling each micromirror of the MMAL independently without macroscopic movements of the endoscope body or parts thereof.

Still another objective of the invention is to provide an imaging device that can compensate the aberration caused by optical effects due to the medium between the object and its image or defects of a lens system that leads its image to deviate from the rules of paraxial imagery, by controlling each micromirror independently. The present imaging device produces a sharp image through entire area without blurring or vignetting.

Still another objective of the invention is to provide a small and compact imaging device in order to have an endoscope body with a small diameter, which allows a minimal invasive endoscopic procedure. Unlike conventional stereo vision systems that require at least two camera systems, the present invention can determine three-dimensional information using only a single camera system, and this renders a simpler camera calibration and a more compact imaging device. Further, since the MMAL can be made to have a small aperture and the magnification and optical axis can be adjusted without macroscopic movements of the lens system, the endoscope imaging system of the present invention can be made small and compact.

The three-dimensional endoscope imaging device of the present invention has the following advantages: (1) the device provides a set of in-focus depthwise images with depth information and/or an all-in-focus image with depth information representing an object at a given moment; (2) the device has a large range of depth; (3) the device has a high optical efficiency; (4) the device corrects aberration; (5) the device can have high depth resolution; (6) the device has a variable field of view; (7) the device has a variable optical axis; (8) the cost is inexpensive because the MMAL is inexpensive; (9) the device has a very simple structure because there is no macroscopic mechanical displacement or deformation of the MMAL; (10) the device is small and compact; (11) the device requires small power consumption when the MMAL is actuated by electrostatic force.

Other objectives of the invention are to provide a three-dimensional display device that has a simple construction and realistic image representation, to provide a three-dimensional display device and method that utilize a set of depthwise images, to provide a three-dimensional display device that can display a large range of image depth, to provide a three-dimensional display device that comprises two-dimensional/three-dimensional compatibility, and to provide a three-dimensional display device that has a large size variation. Three-dimensional display using the MMAL is proposed in the U.S. patent application Ser. No. 10/778,281 filed Feb. 13, 2004 and U.S. patent application Ser. No. 10/979,624 filed Nov. 2, 2004.

The three-dimensional image display device of the present invention has the following advantages: (1) since the three-dimensional display device actually generates three-dimensional images in the space, the device does not suffer from the disadvantage of prior art device using parallax including imaging difficulties due to considerations for arbitrary distribution of the viewer's position, and binocular disparity due to deviations in the distance between the two eyes, vergence, accommodation, watching by more than one viewers, and the relative position change of the three-dimensional image due to viewer's movement; (2) the cost for providing three-dimensional image data is inexpensive since the data needs only depth information in addition to two-dimensional image information, and thus there is no significant increase in data amount; and (3) the device can be easily converted to a two-dimensional display and vice versa.

Although the present invention is briefly summarized herein, the full understanding of the invention can be obtained by the following drawings, detailed description, and appended claims.

DETAILED DESCRIPTION OF THE ILLUSTRATED EMBODIMENTS

Figure 1:
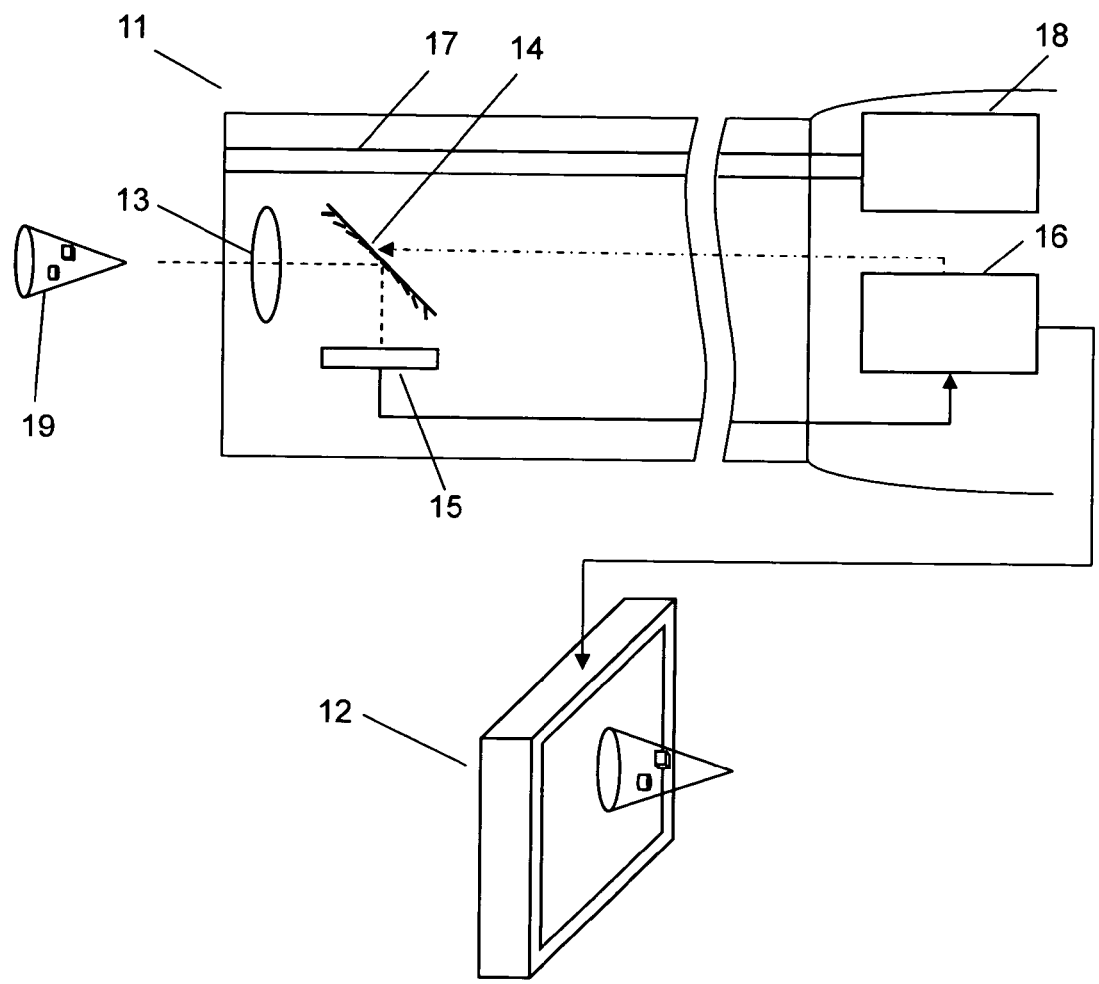
FIG. 1 is a schematic illustration of an endoscope system with a variable optical axis.

FIG. 1 schematically illustrates an endoscope system with a variable optical axis according to the one embodiment of the present invention. The endoscope device comprises an endoscope imaging device 11 and a three-dimensional display device 12. The endoscope imaging device 11 comprises a lens system 13, 14, an imaging unit 15, and an image processing unit 16. The lens system includes an objective lens 13, and a variable focal length MMAL 14, optically coupled to the objective lens 13, configured to change the focal plane by changing the focal length of the MMAL 14. The light delivery system 17 with a light source 18 illuminates an object of interest 19. The imaging unit 15 receives two-dimensional images of an object 19 with different focal planes that are shifted by changing the focal length of the variable focal length MMAL 14. The image depth of the focal plane is obtained from the focal length of the variable focal length MMAL. The image processing unit 16 extracts substantially in-focus pixels or areas from original two-dimensional images taken at different focal planes to generate in-focus depthwise images and provides depth information of the object of interest 19. A set of in-focus depthwise images taken at different focal lengths with a fast imaging rate represents the object at a given moment. The image processing unit 16 can generate an all-in-focus image with depth information as well. By controlling individual micromirrors of the variable focal length MMAL 14, the optical axis can be adjusted, as will be explained in FIG. 4. The imaging device is communicatively connected to the three-dimensional display device. Since the focal plane and the optical axis of the MMAL can be changed without macroscopic movements, the arrangement of optical elements in FIG. 1 requires a small space and allows a compact size endoscope imaging system, which is desirable to achieve a minimal invasive endoscopic procedure.

Figure 2:
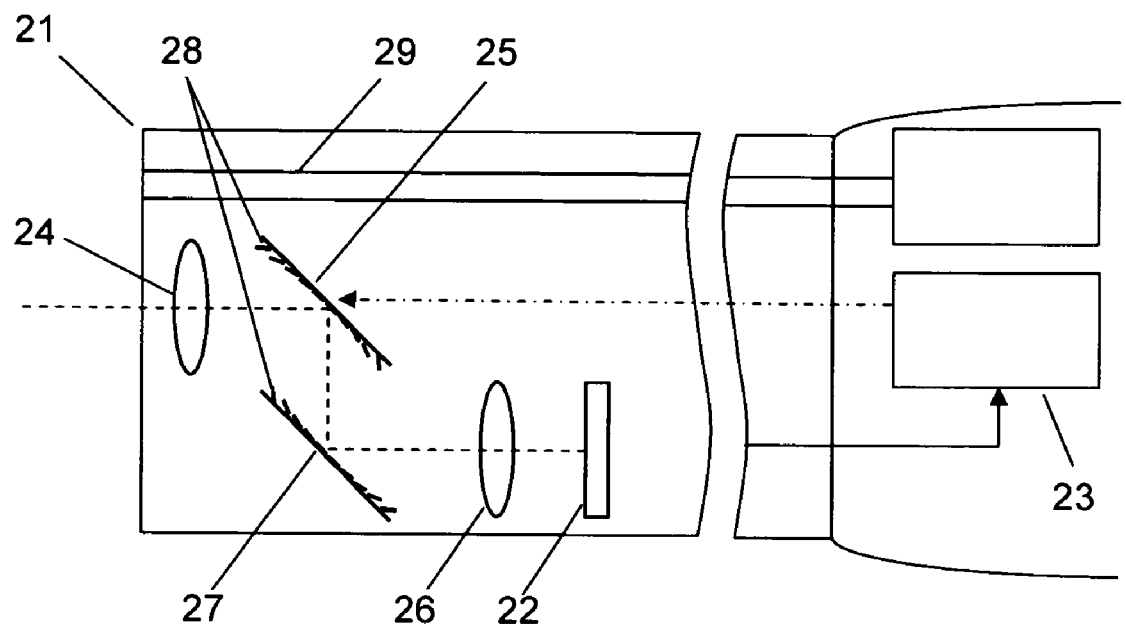
FIG. 2 is a schematic illustration of an endoscope system with a variable optical axis and a variable magnification (a variable field of view)

To provide the microscopic observation of the object, additional variable focal length MMALs can be employed. FIG. 2 illustrates an endoscope imaging device with a variable length MMALs can be employed. FIG. 2 illustrates an endoscope imaging device with a variable optical axis and a variable magnification (a variable field of view) according to the other embodiment of the present invention. The endoscope imaging device 21 comprises a lens system, an imaging unit 22, and an image processing unit 23. The lens system comprises an objective lens 24, and a variable focal length MMAL 25, optically coupled to the objective lens 24, configured to change the focal plane by changing the focal length of the MMAL 25. The lens system also comprises an auxiliary lens 26 or group of lenses to change the field of view and image resolution. Further, the lens system comprises one or more auxiliary lenses for increasing the numerical aperture of the imaging system.

The lens system can comprise the second variable focal length MMAL 27 for the variable magnification of the object. The first and second variable focal length MMAL 25, 27 are optically coupled. They are controlled to change the magnification of the object (size of field of view), wherein the image of an object is optically magnified and to change the focal plane to form two-dimensional images in-focus at a given magnification. The objective lens 24 and the auxiliary lens 26 provide additional magnification. The magnification is adjusted without macroscopic movements of the lens system or time delay since each micromirror 28 of the variable focal length MMALs 25 and 27 is adjusted independently and actuated by electrostatic and/or electromagnetic force.

The image processing unit 23 generates a set of in-focus depthwise image with depth information or an all-in-focus image with depth information using the two-dimensional images with depth information received from the imaging unit 22. The variable focal length MMAL 25 and 27 changes their focal lengths so fast that the imaging processes are achieved faster than the persistence rate of the human eye.

The light delivery system 29 illuminates an object of interest. Further, by controlling individual micromirrors of variable focal length MMALs, the optical axis of the lens system can be adjusted, as will be explained in FIG. 4. Since the MMAL can be made to have a small aperture and the magnification and optical axis can be adjusted without macroscopic movements of the lens system, the arrangement of optical elements in FIG. 2 requires a small space and allows a compact size endoscope imaging system, which is desirable to achieve a minimal invasive endoscopic procedure.

Figure 3:
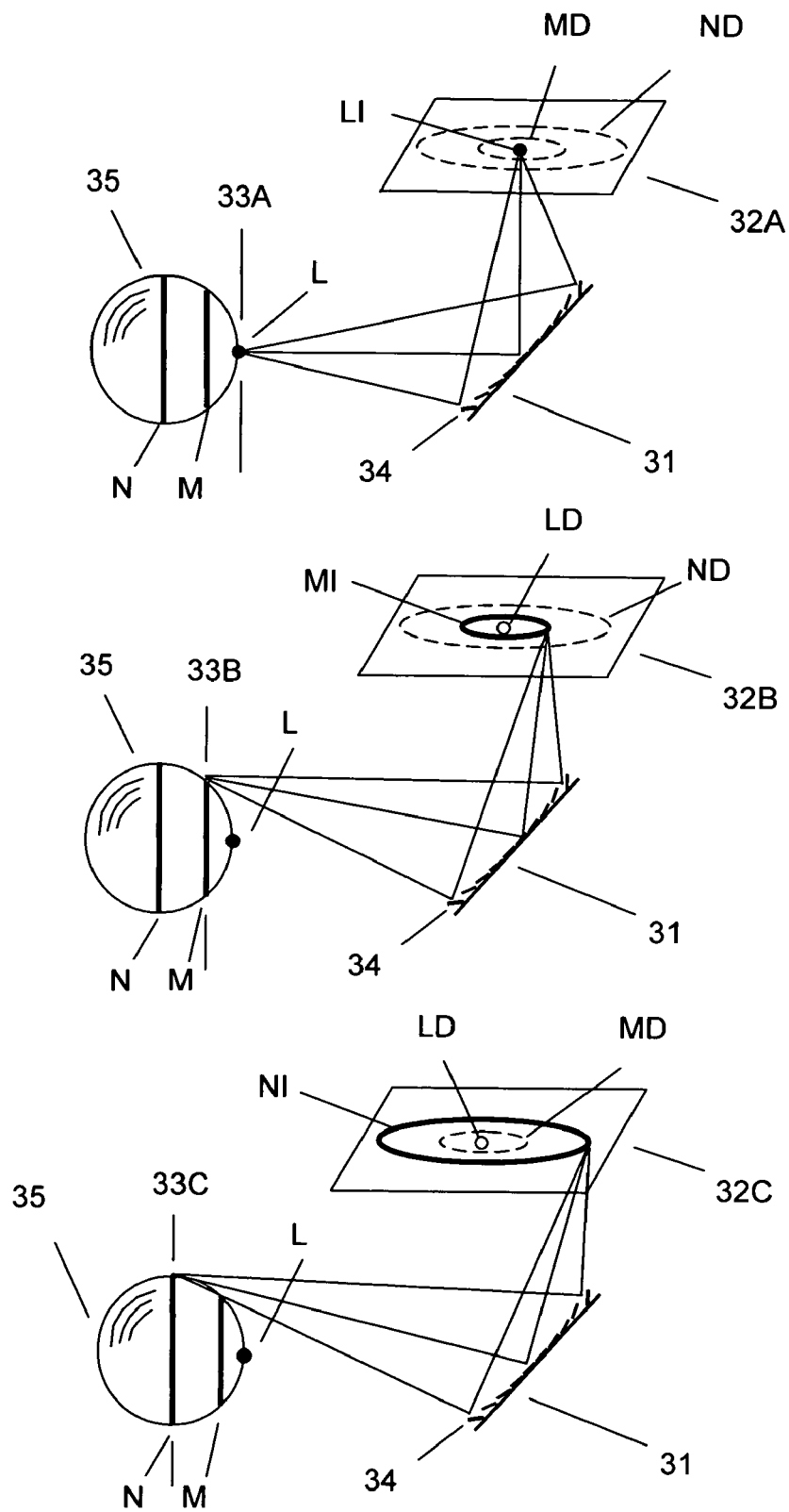
FIG. 3 is a schematic diagram showing how in-focus depthwise images are obtained from two-dimensional images with different focal planes.

FIG. 3 shows how a MMAL 31 takes two-dimensional images 32A, 32B, 32C with the focal planes 33A, 33B, 33C. The MMAL 31 comprises a plurality of micromirrors 34. Each micromirror 34 is controlled to change the focal length of the variable focal length MMAL 31. The focal length of the MMAL 31 is changed by rotation and translation of each micromirror 34, which are controlled by electrostatic and/or electromagnetic force. Two-dimensional images 32A, 32B, 32C are taken with the depth information which corresponds to the position of the focal plane. The two-dimensional image 32A has in-focus image LI at the focal plane 33A, which is the image of a portion L of an object 35. Images MD, ND of portions M, N of an object 35 are defocused. The image processing unit determines the in-focus pixels LI from the two-dimensional images 32A. The two-dimensional image 32A with depth information gives in-focus pixels LI corresponding to the focal plane 33A. The two-dimensional images 32B, 32C with the second and third focal plane 33B, 33C are processed in the same manner as the first focal plane 33A to get in-focus images with depth information.

Figure 4A:
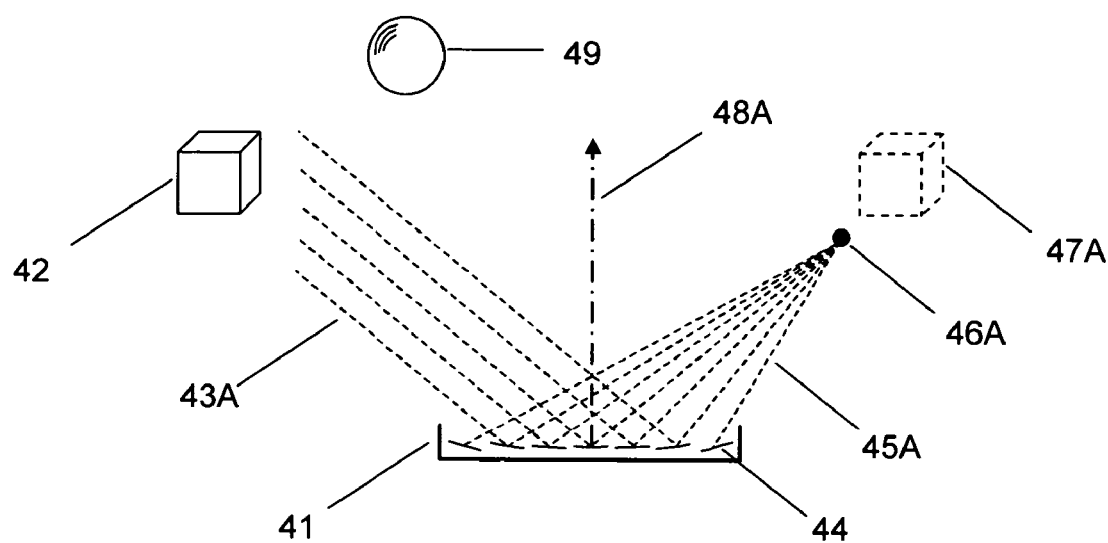
FIG. 4 is a schematic representation for optical axis changes in the MMAL.

The FIG. 4 shows how the optical axis of the MMAL changes. A bunch of light is focused by the MMAL 41. In FIG. 4A, a cube object 42 is imaged onto the image plane. The light 43A from the object 42 is reflected by each of the micromirror 44. The reflected light 45A is focused onto the focal point 46A of the image and finally makes an image of a cube 47A in the image sensor. During the focusing process the optical axis is defined as a surface normal direction 48A of a micromirror 44.

Figure 4B:
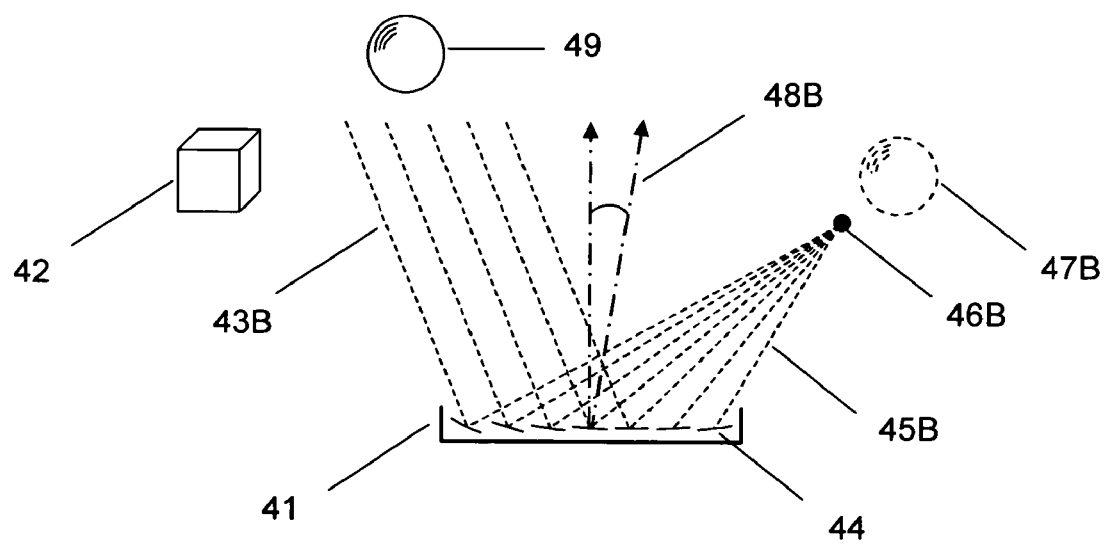

As shown in FIG. 4B, the MMAL can make a different image 47B from a different object 49 without macroscopic movements. By changing the respective angles of the micromirrors 44, this time the MMAL accepts the light 43B from the sphere 49. The reflected light 45B is focused onto a focal point 46B and makes the image of the sphere 47B. This time the optical axis is changed by an angle and becomes the surface normal direction 48B of a micromirror.

FIGS. 5A-5D illustrate the general principle regarding the distance or depth of an image formed by a lens and the focal length of the lens. When the light from an object passes through a lens, it converges or diverges depending on the distance L between the object and the lens, and the focal length of the lens. In the description of the present invention, a lens means an optical element that focuses light, and is not confined to a refractive type lens.

FIGS. 5A-5D demonstrate that the position of a virtual or real image changes according to the focal length of a lens, and the position of the image will change continuously as the focal length varies continuously.

Figure 5A:
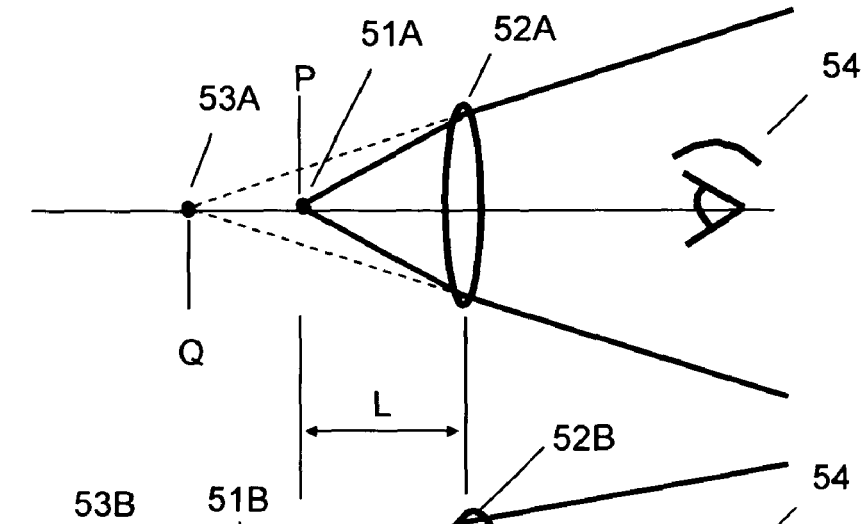
FIGS. 5A-5D are schematic diagrams showing how the depth of an image is changed as the focal length of a lens is changed.
Figure 5B:
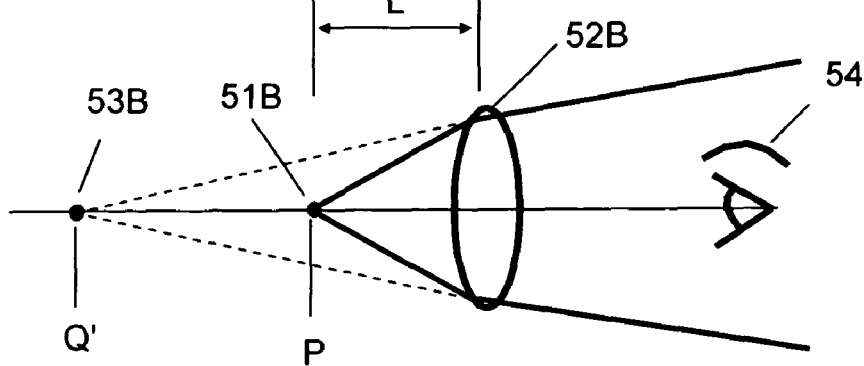

FIG. 5A shows that the light from an object 51A passes through a lens 52A and then diverges with a different angle. FIG. 5B is a similar diagram for a lens 52B having a shorter focal length. The light refracted by the lens 52A, 52B forms a virtual image 53A, 53B. When a viewer 54 sees the refracted light, the viewer perceives the object 51A, 51B, which are positioned at point P, as existing at point Q, Q'.

Figure 5C:
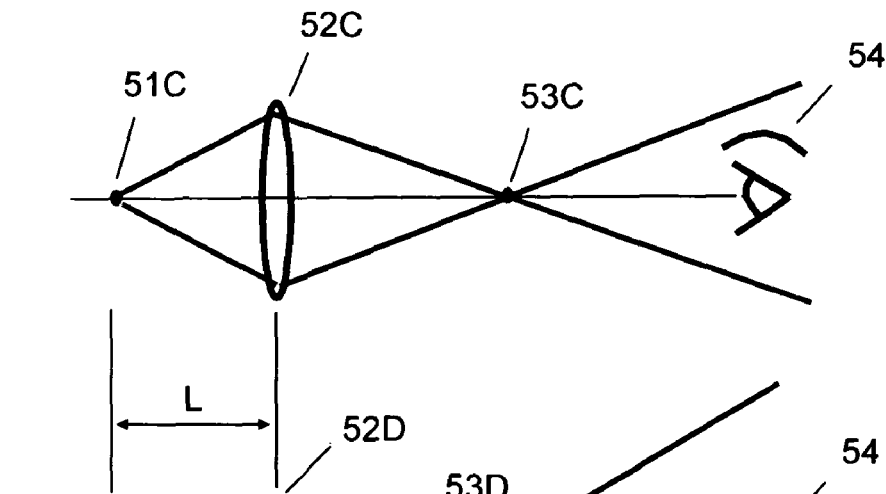
Figure 5D:
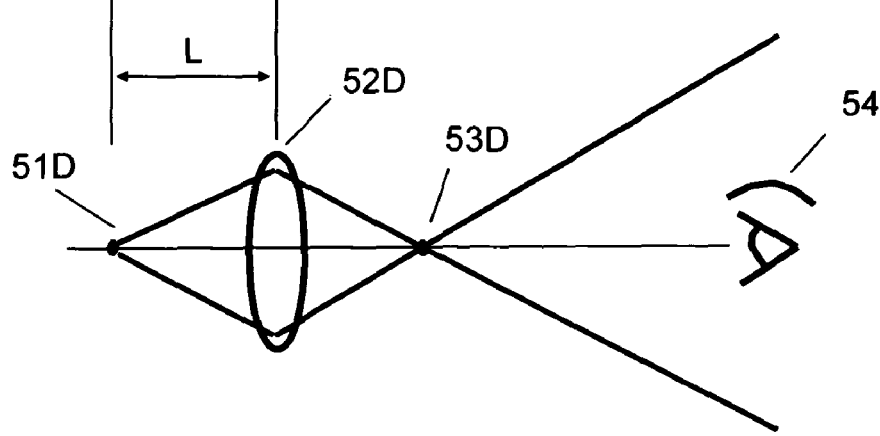

FIG. 5C shows that the light from an object 51C passes through a lens 52C and then converges to form a real image 53C. FIG. 5D is a similar diagram for a lens 52D having a shorter focal length. When the viewer 54 sees an object 51C, 51D through the lens 52C, 52D, the viewer perceives the object 51C, 51D as the real image 53C, 53D.

For a given distance L between the object and the lens, the position of the image formed by the lens varies depending on the focal length of the lens. The position of the image can be calculated with Gaussian lens formula. FIGS. 5A and 5B show that the virtual image 53A is nearer to the viewer 54 with the lens 52A having a longer focal length, and the virtual image 53B is farther from the viewer 54 with the lens 52B having a shorter focal length. FIGS. 5C and 5D show that the real image 53C is nearer to the viewer 54 with the lens 52C having a longer focal length, and the real image 53D is farther from the viewer 54 with the lens 52D having a shorter focal length.

Figure 6:
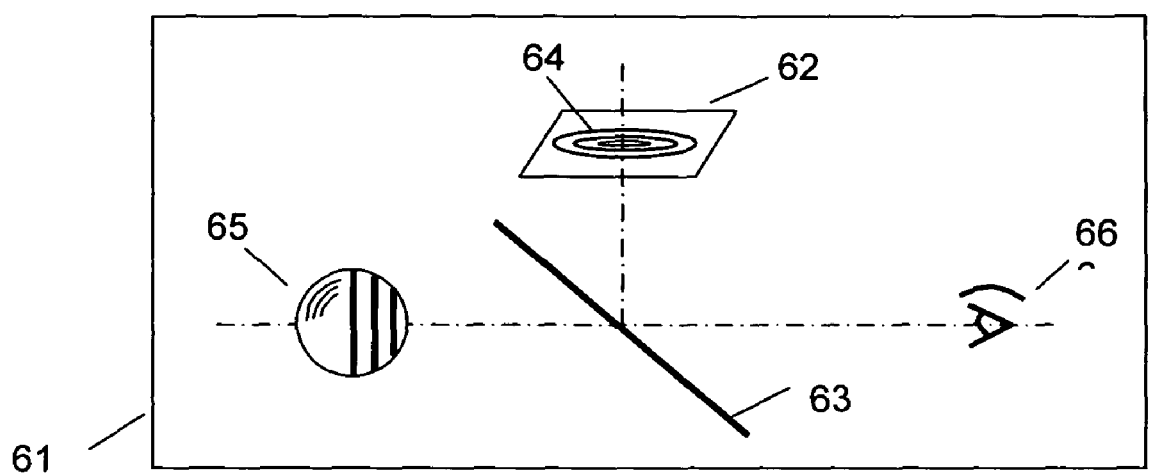
FIG. 6 is a schematic diagram showing a three-dimensional display device of the present invention.

FIG. 6 schematically shows a three-dimensional display device 61 according to one embodiment of the present invention. The three-dimensional display device 61 includes a two-dimensional display 62 and a variable focal length MMAL 63. The two-dimensional display 62 displays one in-focus depthwise image 64 at a time, which is received from the image processing unit 16 (or 27) or a storage space of the three-dimensional imaging system. The two-dimensional display 62 displays only pixels that should be imaged at the same depth at a given frame. The variable focal length MMAL 63 receives light from the two-dimensional display 62 and forms a corresponding image at the required location in the space to generate a three-dimensional image. The location of the image formed in the space depends on depth information of the in-focus depthwise image, received from the image processing unit 16 (or 27) or the storage space of the three-dimensional imaging system, and is adjusted by changing the focal length of the variable focal length MMAL. The variable focal length MMAL 63 are synchronized with the two-dimensional display 62 so that the variable focal length MMAL 63 can have a focal length corresponding to the depth information of the in-focus depthwise image 64 displayed in the two-dimensional display 62. As a set of in-focus depthwise images representing an object are sequentially displayed in the two-dimensional display 62, an three-dimensional image 65 of the object is formed in the space accordingly and perceived as three-dimensional by a viewer 66.

Figure 7A:
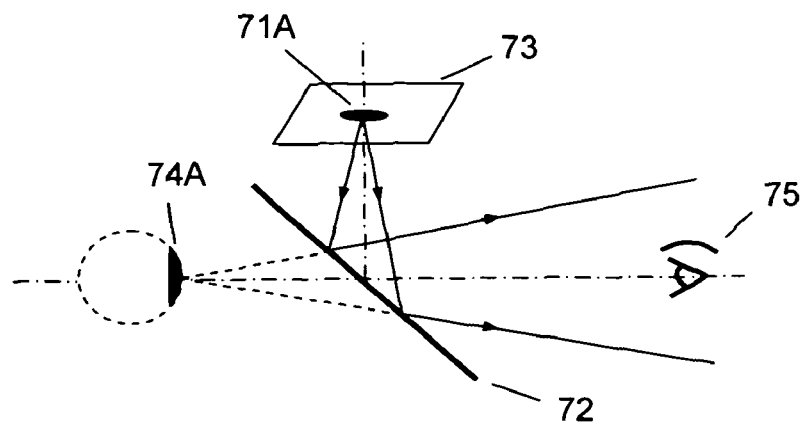
FIGS. 7A-7C are schematic diagrams showing how a two-dimensional display and a variable focal length MMAL displays three-dimensional images.
Figure 7B:
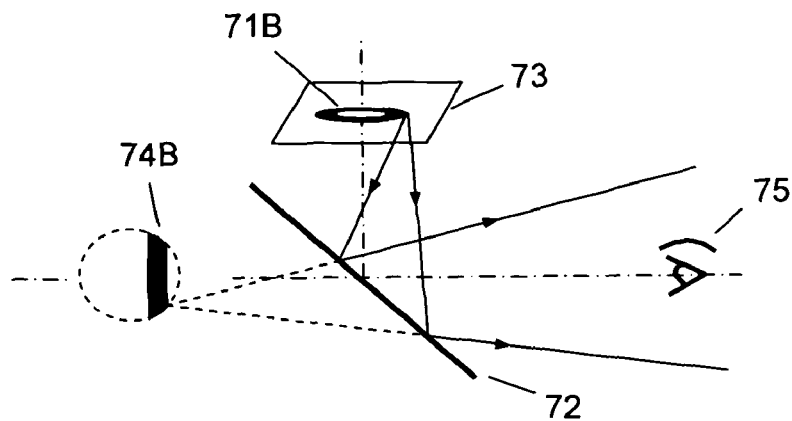
Figure 7C:
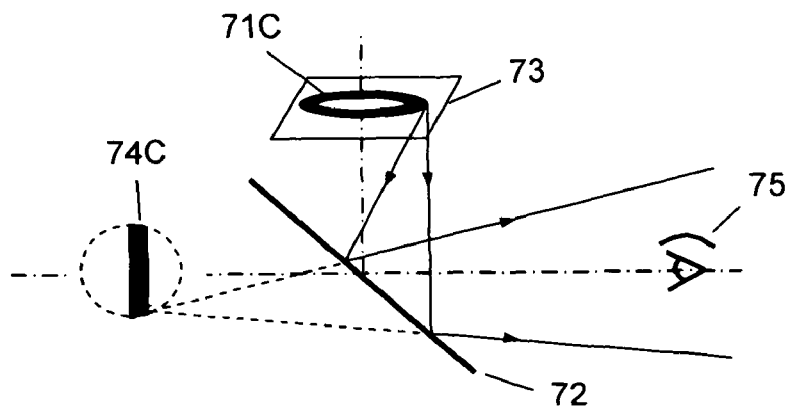

FIGS. 7A-7C show how a two-dimensional display and a variable focal length MMAL displays three-dimensional images. At a given moment, an object is represented by a set of in-focus depthwise images 71A, 71B, 71C, each of which represents a portion of the object having the same image depth. The number of in-focus depthwise images representing the object at a given moment (number of depths) depends on the depth resolution requirement, the refresh rate of the two-dimensional display 73, and the focusing speed of the variable focal length MMAL 72 and may increase for a better image quality. The two-dimensional display 73 displays one in-focus depthwise image at a time. The variable focal length MMAL 74 receives light from the two-dimensional display 73 and forms a corresponding image 74A, 74B, 74C at the required location in the space to generate a three-dimensional image. The set of in-focus depthwise images representing the object at a given moment are sequentially displayed in the two-dimensional display 73 within a unit time. In order to have realistic three-dimensional video images in the space for the view 75, focusing speed of the variable focal length MMAL 72 and refresh rate of the two-dimensional display 73 must be equal or greater than the product of the persistent rate of the human eye and the number of depths.

For example, assume that the persistent rate of the human eye is 30 Hz and the number of depths is 10. In order to have realistic three-dimensional video images in the space, the focusing speed of the variable focal length MMAL and the refresh rate of two-dimensional display are at least equal to 300 Hz, respectively. The variable focal length MMAL 72 of the present invention is capable of changing the focal length fast enough to generate realistic three-dimensional video images.

Figures 8A, 8B:
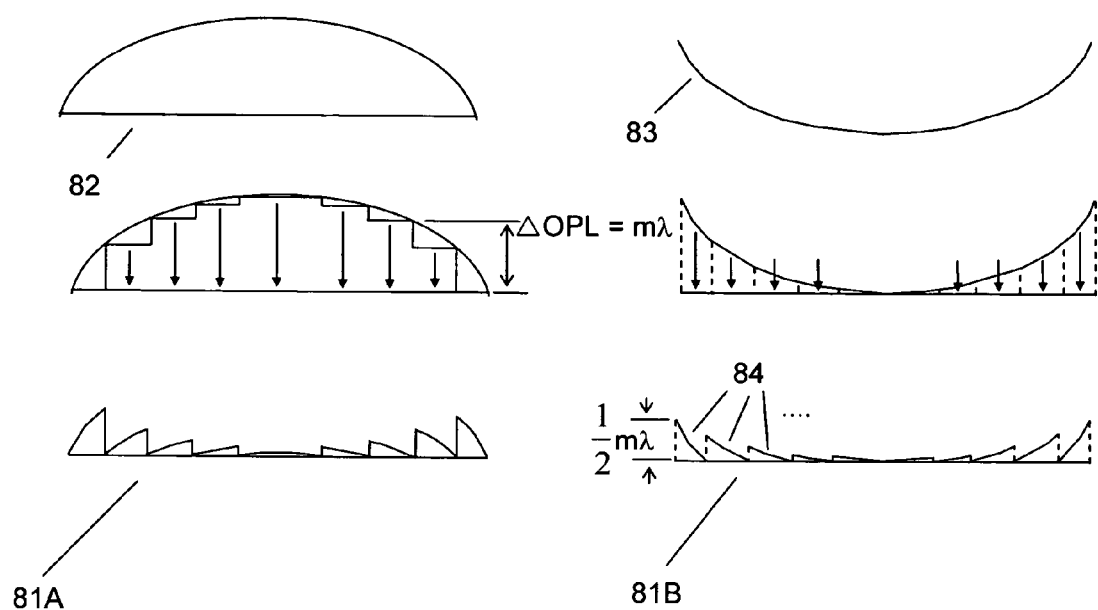
FIG. 8A is a schematic diagram showing how a refractive Fresnel lens replaces an ordinary single-bodied lens.
FIG. 8B is a schematic diagram showing how a reflective Fresnel lens replaces an ordinary single-bodied mirror.

FIG. 8A schematically shows how a refractive Fresnel lens 81A replaces an ordinary single-bodied lens 82. FIG. 8B shows how a reflective Fresnel lens 81B, replacing an ordinary single-bodied mirror 83, is formed with a MMAL. The MMAL includes a plurality of micromirrors 84, and each micromirror 84 is controlled to form a reflective Fresnel lens 81B and to change the focal length of the lens.

In order to obtain a bright and sharp image, the variable focal length MMAL must meet the two conditions for forming a lens. One is that all the rays should be converged into the focus, and the other is that the phase of the converged rays must be the same. Even though the rays have different optical path lengths, the same phase condition can be satisfied by adjusting the optical path length difference to be integer multiples of the wavelength of the light. Each facet converges rays to one point, and rays refracted or reflected by different facets have an optical path length difference of integer multiples of the incident light.

To change the focal length of the MMAL, the translational motion and/or the rotational motion of each of the micromirrors are controlled to change the direction of light and to satisfy the phase condition of the light.

The variable focal length MMAL is also an adaptive optical component compensating the aberration of the imaging system by controlling the translational motion and/or the rotational motion of each micromirror.

Figures 9A, 9B:
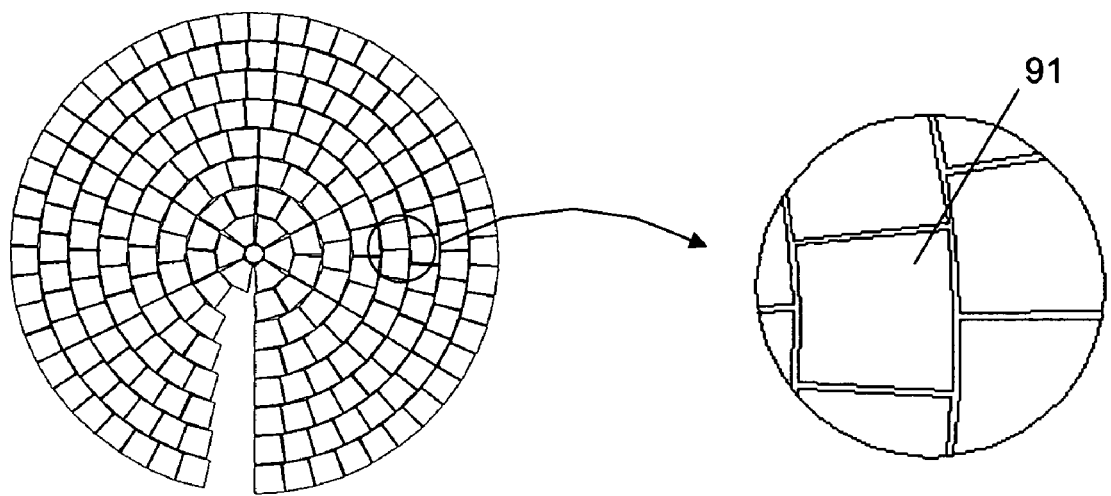
FIG. 9A is a schematic plan view showing a variable focal length MMAL that is made of many micromirrors.
FIG. 9B is an enlarged detail plan view of the micromirrors.

FIGS. 9A and 9B show that the micromirrors 91 are arranged to form many concentric circles. The micromirrors 91 are arranged in a flat plane as shown in FIG. 8B.

The variable focal length MMAL must meet the following requirements to be used in three-dimensional display and imaging system. First, it must have a focal length change speed fast enough for three-dimensional display. Second, it must have a large range of numerical aperture change, since the depth range that can be imaged depends on the range of numerical aperture change. Third, it needs to have a large diameter depending on constructions of three-dimensional displays.

The MMAL meets three requirements. The response speed of the micromirror 91 exceeds the persistent rate of the human eyes times the number of depths unless the depth resolution requirement is extremely high. It is possible to make the focal length change within hundreds of micro-seconds. The range of numerical aperture change of the MMAL is large since the range of focal length variation of the MMAL is large. So, the MMAL can have a greater range of image depths, which is an essential requirement for a three-dimensional display. Also, the MMAL can have a large diameter. In contrast with a lens having a continuous shape, for which it becomes difficult to make an ideal curved surface as the size becomes larger, there is no difficulty in enlarging the size of MMAL, since the MMAL comprises discrete micromirrors.

Since the MMAL is a reflective lens, the optical system of the three-dimensional display device cannot be aligned in a line. An optical arrangement, in which the reflected light is not blocked by the two-dimensional display, is required.

Figure 10:
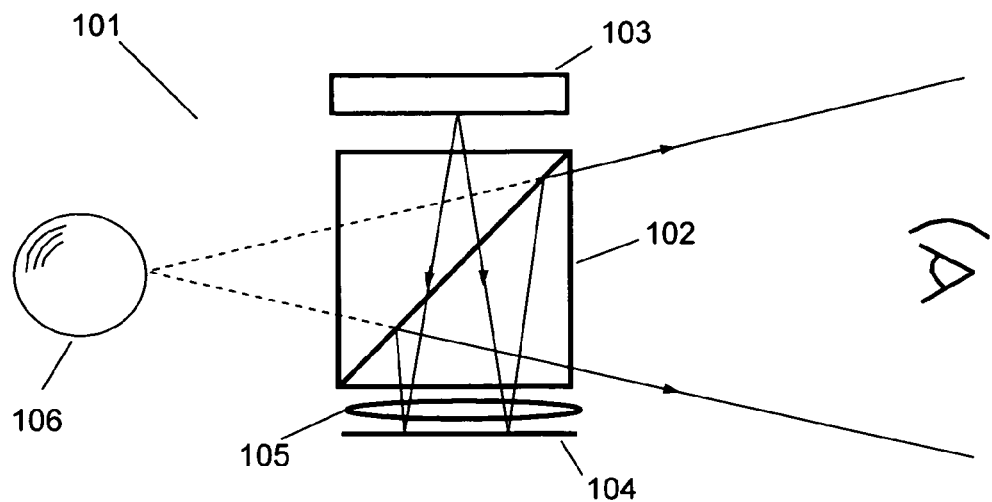
FIG. 10 is a schematic diagram showing a beam splitter and an auxiliary lens added to the three-dimensional display device.

FIG. 10 shows an arrangement in which the three-dimensional display device 101 further includes a beam splitter 102 positioned in the path of light between a two-dimensional display 103 and a variable focal length MMAL 104. The two-dimensional display 103 and the variable focal length MMAL 104 are arranged parallel with each other. The beam splitter 102 changes the direction of the light by 90°, and thus simulating an in-line optical arrangement. The MMAL is positioned perpendicular to the light path.

Alternatively, referring back to FIG. 6, the variable focal length MMAL 63 is positioned so that the path of the light reflected by the variable focal length MMAL 63 is not blocked by the two-dimensional display 62. The arrangement in FIG. 6 has advantages of simple structure and wider field of view since the distance between the two-dimensional display and the variable focal length MMAL 63 is closer than that of the arrangement with the beam splitter 102. However, it needs special consideration of the correction of the aberration induced by the obliquely positioned variable focal length MMAL 63. The choice of either arrangement depends on the use of the display device.

As shown in FIG. 10, the three-dimensional display device may further include an auxiliary lens 105 having a predetermined focal length and positioned adjacent to the variable focal length MMAL 104. The three-dimensional image 106 is formed by the effective focal length of the variable focal length MMAL 103 and the auxiliary lens 105. With the auxiliary lens 105, the variable focusing range of the three-dimensional display device can be extended or changed to a desired range. A refractive type Fresnel can be used as an auxiliary lens 105.

Figure 11:
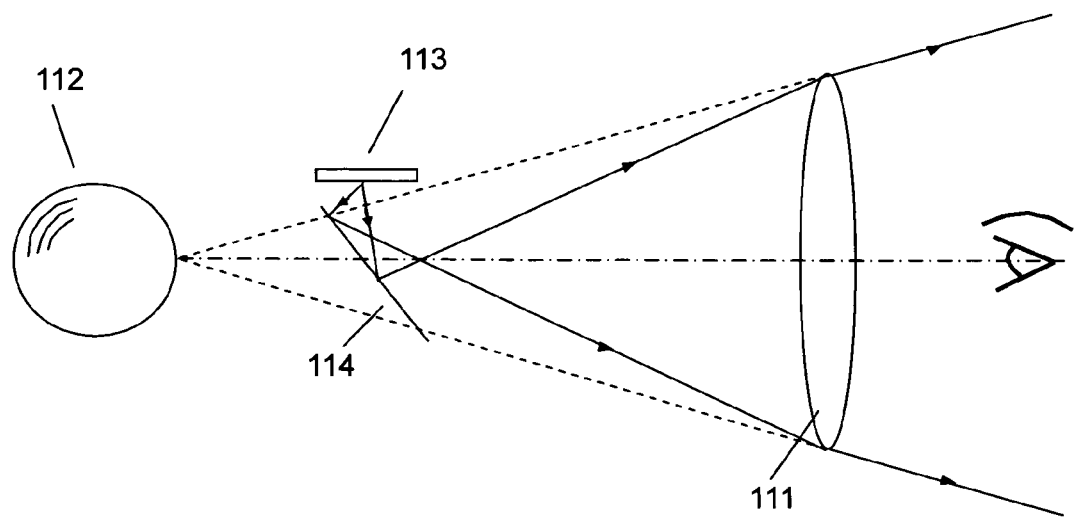
FIG. 11 is a schematic diagram showing a magnifying lens added to the three-dimensional display device.

As shown in FIGS. 6 and 10, the variable focal length MMALs 63, 104 should have the size of the screen. For a device having a large display screen, it is almost impossible or extremely expensive to make a variable focal length MMAL having a size as large as that of the screen. FIG. 11 shows that the three-dimensional display device may further include an auxiliary lens 111 that magnifies the three-dimensional image 112, in order to overcome the limitation in size. The auxiliary lens 111 may be an ordinary refractive lens or a refractive Fresnel lens. The screen size becomes the size of the auxiliary lens 111, which has a fixed focal length. A two-dimensional display 113 and a variable focal length MMAL 114 can have a compact size that is much smaller than the size of the auxiliary lens 111. The effective focal length of the three-dimensional display device is varied by changing the focal length of the variable focal lens 114.

The focal length of the variable focal length MMAL 114 may be controlled to be fixed. By fixing the focal length of the variable focusing length and operating the two-dimensional display as a general two-dimensional display device, the three-dimensional display device can be easily converted into a two-dimensional display device. In two-dimensional mode, three-dimensional display shows two-dimensional images at a different distance from the view.

Method for displaying a three-dimensional image may be one using a virtual image as illustrated in FIGS. 5A and 5B, or one using a real image as illustrated in FIGS. 5C and 5D. The method using a real image has an advantage that it enables more realistic display since the image is generated closer to the viewer, and has a disadvantage that the range of display is limited between the viewer and the screen. With the method using a virtual image, the image is generated behind the screen. This method has an advantage that it can display an image having depth ranging from the screen to the infinity.

Figure 12A:
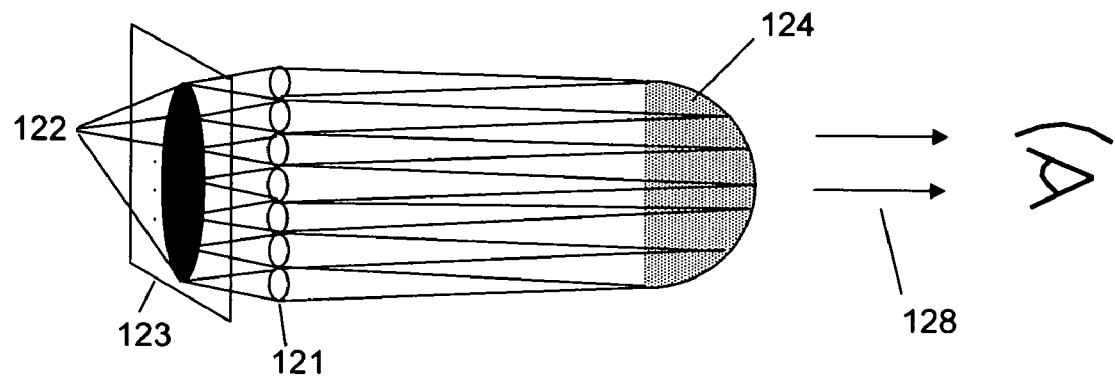
FIG. 12A is a schematic diagram showing a three-dimensional display device, which has variable focal length lenses corresponding to pixels of a two-dimensional display.
Figure 12B:
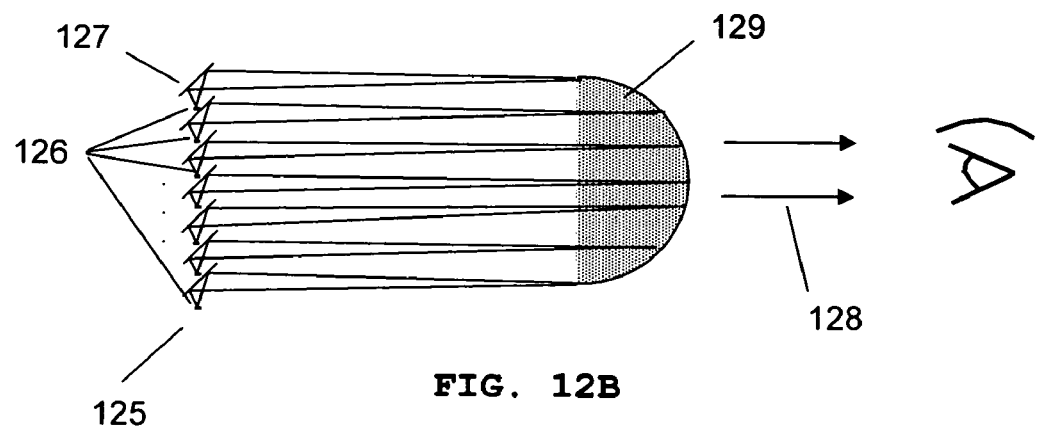
FIG. 12B is a schematic diagram showing that the MMAL is used as the variable focal length MMAL for the device of FIG. 12A.

FIGS. 12A and 12B show a three-dimensional display device according to the other embodiment of the present invention. FIG. 12A shows how a three-dimensional display device, which has many variable focal length lenses 121 corresponding to pixels 122 of a two-dimensional display 123, operates to display a three-dimensional image 124. The partial image displayed by each pixel 122 is imaged at its image depth by the variable focal length lens 121 corresponding to the pixel 122. Since the partial image displayed by each pixel is individually handled by the corresponding variable focal length lens, dividing an image into depthwise images and displaying the depthwise images are not required, and thus this embodiment does not need a high speed two-dimensional display or a high speed variable focal length lens. A two-dimensional display having a usual speed can be used. The size of the variable focal length lens 121 is similar to that of the pixel 122.

FIG. 12B shows schematically a three-dimensional display device 125. The three-dimensional display device 125 includes a two-dimensional display having a plurality of pixels 126, and a plurality of variable focal length MMALs 127. Each of the variable focal length MMALs 127 corresponds to each of the pixel 126. The focusing speed of the variable focal length MMAL 127 is at least persistent rate of the human eyes and each of the variable focal length MMALs 127 reflect light from the two-dimensional display. The focal length of each of the variable focal length MMALs 127 changes according to the image depth of an image displayed by each of the pixels 126.

Since the MMAL is a reflective optical element, the lens element 127 is positioned so that the reflected light is not blocked by the two-dimensional display. Each of the pixels 126 displays a portion of an all-in-focus image in a direction orthogonal with the device display direction 128 of the three-dimensional display device 125. The all-in-focus image is received from the image processing unit 16 (or 27) or a storage space of the three-dimensional imaging system. Each of the lens elements 127 is positioned at an angle of 45° with respect to the display direction of the pixels 126 and the device display direction 128. A three-dimensional image 129 is formed by the lens elements 127. Notwithstanding this complex arrangement, the MMAL is used because its range of numerical aperture change is large.

Figure 13:
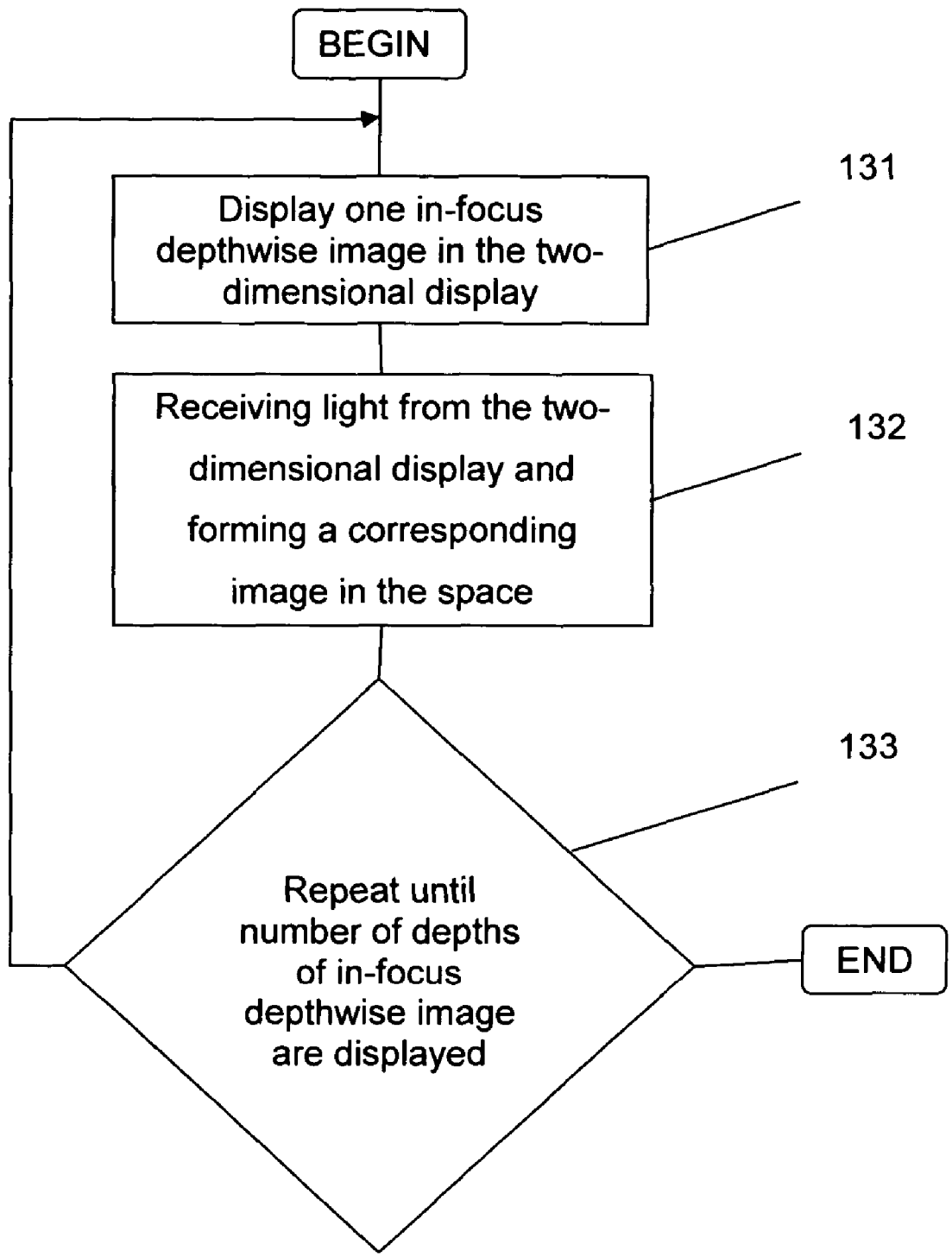
FIG. 13 is a flow diagram showing a three-dimensional display method of the present invention.

FIG. 13 shows a three-dimensional display method according to the invention. In step 131, an in-focus depthwise image is displayed in a two-dimensional display. Then in step 132, the corresponding image is formed in the space by receiving light from the two-dimensional display and reflecting the light to the required location using depth information of the in-focus depthwise image. In step 133, steps 131 and 132 are repeated for the number of depths within a unit time. Each of in-focus depthwise images represents the portion of an object having the same image depth. As a set of in-focus depthwise images representing the object at a given moment are sequentially displayed by the above steps, a three-dimensional image is formed in the space accordingly. In order to have realistic three-dimensional video images, the focusing speed of a variable focal length lens is at least equal to the product of the persistent rate of the human eye and the number of depths.

The step of forming three-dimensional image 132 is performed with a variable focal length MMAL.

While the invention has been shown and described with reference to different embodiments thereof, it will be appreciated by those skills in the art that variations in form, detail, compositions and operation may be made without departing from the spirit and scope of the invention as defined by the accompanying claims.

What is claimed is:

1. A three-dimensional endoscope system comprising a three-dimensional imaging device comprising:
   a) a lens system comprising an objective lens and at least one variable focal length MMAL optically coupled to the objective lens, wherein the variable focal length MMAL comprises a plurality of micromirrors and each micromirror of the variable focal length MMAL is controlled independently, wherein the variable focal length MMAL is configured to change a focal plane by changing a focal length of the variable focal length MMAL;
   b) an imaging unit, optically coupled to the lens system, configured to receive an two-dimensional image from the lens system and to sense the two-dimensional image; and
   c) an image processing unit, communicatively coupled to the imaging unit, configured to process the two-dimensional image sensed by the imaging unit and to generate in-focus depthwise images with depth information.

2. The three-dimensional endoscope system of claim 1, further comprising a three-dimensional display device, communicatively coupled to the three-dimensional imaging device to receive image data and its depth information, comprising at least one variable focal length MMAL.

3. The three-dimensional endoscope system of claim 1, wherein a set of the depthwise images with depth information can be displayed by various conventional three-dimensional display devices through geometric data transformation.

4. The three-dimensional endoscope system of claim 1, wherein the focal plane of the lens system is changed by change of the focal length of the variable focal length MMAL.

5. The three-dimensional endoscope system of claim 1, wherein the imaging unit comprises one or more two-dimensional image sensors taking the two-dimensional image at each focal plane.

6. The three-dimensional endoscope system of claim 1, wherein the lens system with variable focal length MMAL further comprises an auxiliary lens or group of lenses to change the field of view and the image resolution.

7. The three-dimensional endoscope system of claim 1, wherein the lens system further comprises one or more auxiliary lenses for increasing the numerical aperture of the three-dimensional imaging device.

8. The three-dimensional endoscope system of claim 1, wherein the lens system with variable focal length MMAL further comprises another variable focal length MMAL for variable magnification of the object.

9. The three-dimensional endoscope system of claim 1, wherein the image processing unit generates an all-in-focus image with depth information using the two-dimensional images with depth information received from the imaging unit.

10. The three-dimensional endoscope system of claim 1, wherein imaging processes in the three-dimensional imaging device are achieved faster than a persistent rate of human eyes.

11. The three-dimensional endoscope system of claim 1, wherein each micromirror of the variable focal length MMAL is controlled to change the focal length of the variable focal length MMAL.

12. The three-dimensional endoscope system of claim 1, wherein the variable focal length MMAL is made to have a small aperture for a minimal invasive endoscopic procedure.

13. The three-dimensional endoscope system of claim 1, wherein the variable focal length MMAL is an adaptive optical component compensating aberration of the three-dimensional endoscope system.

14. The three-dimensional endoscope system of claim 1, wherein the variable focal length MMAL changes its optical axis to find an object of interest without macroscopic movements of a body or parts of the three-dimensional endoscope system.

15. The three-dimensional endoscope system of claim 1, further comprising at least one light delivery system for illuminating an object of interest.

16. The three-dimensional endoscope system of claim 2, wherein the three-dimensional display device comprises:
 a) a two-dimensional display displaying an in-focus depthwise image; and
 b) a variable focal length MMAL receiving light from the two-dimensional display and forming a corresponding image of the in-focus depthwise image at the required location in the space using depth information of the in-focus depthwise image.

17. The three-dimensional endoscope system of claim 16, wherein the two-dimensional display shows one in-focus depthwise image at a time.

18. The three-dimensional endoscope system of claim 16, wherein the in-focus depthwise image and depth information thereof are received from the three-dimensional imaging device.

19. The three-dimensional endoscope system of claim 16, wherein the variable focal length MMAL in the three-dimensional display device changes its focal length to form the three-dimensional image.

20. The three-dimensional endoscope system of claim 16, wherein the variable focal length MMAL in the three-dimensional display device are synchronized with the two-dimensional display so that the variable focal length MMAL in the three-dimensional display device can have a focal length corresponding to the depth information of the in-focus depthwise image displayed in the two-dimensional display.

21. The three-dimensional endoscope system of claim 16, wherein the three-dimensional display device further comprises a beam splitter positioned in the path of light between the two-dimensional display and the variable focal length MMAL in the three-dimensional display device.

22. The three-dimensional endoscope System of claim 16, wherein the variable focal length MMAL in the three-dimensional display device is positioned so that the path of the light reflected by the variable focal length MMAL in the three-dimensional display device is not blocked by the two-dimensional display.

23. The three-dimensional endoscope system of claim 16, wherein the three-dimensional display device further comprises an auxiliary lens for increasing the size of the screen.

24. The three-dimensional endoscope system of claim 16, wherein the focal length of the variable focal length MMAL in the three-dimensional display device can be fixed to display two-dimensional information.

25. The three-dimensional endoscope system of claim 2, wherein the three-dimensional display device comprises:
 a) a two-dimensional display comprising a plurality of pixels, and
 b) a plurality of variable focal length MMALs, wherein each of the variable focal length MMAL corresponds to each of the pixel.

26. The three-dimensional endoscope system of claim 25, wherein each of the variable focal length MMAL in the three-dimensional display device reflects the light from the corresponding pixel of the two-dimensional display.

27. The three-dimensional endoscope system of claim 25, wherein the each pixel of the two dimensional display and the corresponding variable focal length MMAL in the three-dimensional display device is synchronized.

28. The three-dimensional endoscope system of claim 25, wherein the each pixel of the display is displayed and light from the pixel is focused by the variable focal length MMAL in the three-dimensional display device according to the corresponding depth information.

29. The three-dimensional endoscope system of claim 25, wherein the each pixel of the two-dimensional display is displayed and the focal length of the variable focal length MMAL in the three-dimensional display device is changed at least at the persistent rate of the human eye.

30. The three-dimensional endoscope system of claim 9, wherein the all-in-focus image with depth information can be displayed by various conventional three-dimensional display devices through geometric data transformation.

* * * * *